United States Patent [19]
Miki et al.

[11] Patent Number: 5,885,788
[45] Date of Patent: Mar. 23, 1999

[54] METHOD FOR MEASURING AN AMOUNT OF LDL-CHOLESTEROL

[75] Inventors: Yutaka Miki; Nobuko Imajo; Toshiro Hanada, all of Amagasaki, Japan

[73] Assignee: Wako Pure Chemical Industries, Ltd., Osaka, Japan

[21] Appl. No.: 897,954

[22] Filed: Jul. 24, 1997

[30] Foreign Application Priority Data

Jul. 25, 1996 [JP] Japan .................................. 8-214347

[51] Int. Cl.$^6$ .............. C12Q 1/26; C12Q 1/44; C12Q 1/28; C12Q 1/00
[52] U.S. Cl. ................ 435/25; 435/19; 435/28; 435/4; 435/975; 436/71
[58] Field of Search ................ 435/25, 19, 28, 435/4, 975; 436/71

[56] References Cited

U.S. PATENT DOCUMENTS

| 4,164,448 | 8/1979 | Röeschlau et al. ............ 435/25 |
| 4,544,630 | 10/1985 | Ziegenhorn et al. ............ 435/28 |
| 5,411,870 | 5/1995 | Law et al. ..................... 435/25 |

FOREIGN PATENT DOCUMENTS

| 0 402 094 A | 6/1990 | European Pat. Off. . |
| 0 657 545 A2 | 12/1994 | European Pat. Off. . |
| 195 05 894 A | 8/1996 | Germany . |

OTHER PUBLICATIONS

Derwent WPI—JP-A58-165800—Patent Abstract of Japan.
Derwent WPI—JP-A6-213899—Patent Abstract of Japan.
Derwent WPI—JP-A6-242110—Patent Abstract of Japan.
Derwent WPI—JP-A7-280812—Patent Abstract of Japan.
Derwent WPI—WO 96/28734—Patent Abstract of Japan.

*Primary Examiner*—Louise N. Leary
*Attorney, Agent, or Firm*—Armstrong, Westerman, Hattori, McLeland & Naughton

[57] ABSTRACT

The present invention is to provide a method for measuring an amount of cholesterol in low density lipoproteins (LDL-cholesterol) in a sample specifically at high accuracy and a reagent used in this method, and the present invention can attain such effect that direct measuring an amount of LDL-cholesterol by widely used automatic analyzers can be conducted by using the invention, which has not been possible after known methods.

12 Claims, 18 Drawing Sheets

METHOD FOR MEASURING AN AMOUNT OF LDL-CHOLESTEROL

BACKGROUND OF INVENTION

The present invention relates to a method and a reagent for measuring an amount of cholesterol in low density lipoproteins (hereinafter abbreviated as LDL) which is present in a living sample such as plasma and serum.

A lipid in plasma comprises mainly cholesterol, triglyceride, phospholipid, etc. and those plasma lipid is combined with apoprotein to form lipoproteins which is circulated in blood. The lipoproteins are classified, according to their density, into high density lipoproteins (HDL), LDL, very low density lipoproteins (VLDL) and chylomicrons (CM), etc. Among those lipoproteins, HDL has an action of transporting excess cholesterol stored in tissues to a liver, and thus has an action of preventing an arteriosclerosis, and on the other hand, LDL takes role as a main transporter for cholesterol from a liver to tissues and thus increase of LDL is considered as having close relation with arteriosclerosis.

Therefore, cholesterol in LDL (hereinafter abbreviated as LDL-cholesterol) has been considered to be a risk factor of arteriosclerosis and ischemic cardiopathy (coronary disease) and an amount of cholesterol in LDL is an important factor for diagnosis, remedy and prevention of those diseases.

As methods for measuring an amount of LDL-cholesterol, there have been known a precipitation method, an ultra-centrifugation method, an electrophoresis method, a calculation method based on a calculation equation, etc. Among those known methods, a precipitation method, an ultra-centrifugation method and an electrophoresis method require a pre-treating process for separation of LDL from other unnecessary lipoproteins by a precipitation/centrifugation treatment, an ultra-centrifugation treatment or an electrophoresis treatment, and thus they are accompanied with such problems that troublesome handling is required and it is not possible to conduct direct measurement with the use only of automatic analyzers which have widely been used in clinical tests at present.

Further a calculating method for calculating it from the total cholesterol amount, HDL-cholesterol amount and triglyceride amount, which has been known as Friedewald equation, has such problem that accurate measurement of an amount of LDL-cholesterol cannot be achieved when a sample containing triglyceride in an amount 500 mg/dl or more is used.

Recently, various methods have been developed in order to solve such problems as mentioned above in the known methods. For instance, a method disclosed in JP-A7-280812 (Japanese Patent Publication-Kokai-) is one example thereof. Namely, this method comprises agglutinating LDL with the use of an agglutinating agent and/or an antibody, introducing cholesterol in lipoproteins other than LDL into a separate reaction system which is not involved in the desired quantitative reaction, wherein cholesterol in lipoproteins other than LDL is consumed, then dissolving the agglutinated LDL with the use of a surfactant and/or an inorganic salt to such extent that quantitative analysis can be conducted, and finally subjecting LDL-cholesterol to quantitative analysis reaction and measuring an absorbance of the reaction solution.

However, this method is accompanied with such problem that it requires 3 or 4 kinds of reagents and thus can be applied only a limited kind of automatic analyzers which can conduct measurement with the use of 3 or 4 kinds of reagents, cannot be applied an automatic analyzers which can conduct only measurement with the use of reagents to the number of two. Further, there is such a problem in this method that reproducibility of measurement is decreased because of using 3 or 4 kinds of reagents.

Additionally, there has been such a method as conducting measurement without troublesome pre-treatment, which is disclosed in JP-A 58-165800 (Japanese Patent Publication-Kokai-). However, in this method, usable concentration range of a cholesterol esterase and a surfactant in the reagent is rather limited, and thus preparation of the reagent requires troublesome procedures, and further measuring conditions such as pH and intervals of measurement time have to be adjusted strictly, and in addition, only kinetic measurement of LDL-cholesterol, namely measurement by rate-assay method, can be conducted, because cholesterol also in HDL is involved in the reaction to some extent. For these reasons, this method is not said as practical.

Under the circumstances mentioned above, the problems to be dissolved by the present invention is to provide a method for measuring an amount of LDL-cholesterol in living samples directly with the use of widely used automatic analyzers without conducting troublesome pre-treatment for separation of LDL from unnecessary lipoproteins other than LDL which has been required in the known methods and also to provide a reagent usable in this method.

SUMMARY OF THE INVENTION

The present invention relates to a method for measuring an amount of cholesterol in low density lipoproteins, which comprises conducting the measurement of cholesterol in the presence of an amphoteric surfactant and an aliphatic amine containing carboxyl group(s) or sulfonic acid group(s).

The present invention also relates to a method for measuring an amount of cholesterol in low density lipoproteins of a living sample, which comprises mixing the living sample with a first reagent comprising an aqueous medium, measuring an absorbance (OD1) of a resulting reaction solution, mixing the resulting solution with a second reagent solution containing a cholesterol oxidase and a cholesterol esterase, measuring an absorbance (OD2) of the latter resulting solution, subtracting a value obtained by multiplying OD1 with a correction coefficient from the OD2 to give OD3, applying thus obtained OD3 a calibration curve showing a relation between an amount cholesterol and OD3 which is previously prepared by conducting the above process with the use of a standard specimen containing a predetermined amount of cholesterol, wherein each of an amphoteric surfactant and an aliphatic amine containing carboxyl group(s) or sulfon acid group(s) is incorporated in at least one of the first reagent and the second reagent, and each of a coupler, a developer and a peroxidase is incorporated in at least one of the first reagent and the second reagent.

The present invention further relates to a reagent for measuring an amount of cholesterol in low density lipoproteins, which comprises an amphoteric surfactant and an aliphatic amine containing carboxyl group(s) or sulfonic acid group(s).

The present invention still further relates to a kit for measuring an amount of cholesterol in low density lipoproteins, which comprises a first amount of cholesterol in low density lipoproteins, which comprises a first reagent containing one of a coupler and a developer and a second reagent containing a cholesterol oxidase, a cholesterol esterase, a peroxidase and the other of the coupler and the developer, wherein each of an amphoteric surfactant and an aliphatic amine containing carboxyl group(s) or sulfonic acid group(s) are incorporated in at least one of the first reagent and the second reagent.

Further, the present invention still further relates to a kit for measuring an amount of cholesterol in low density lipoproteins, which comprises a first reagent containing an amphoteric surfactant and one of a coupler and a developer and a second reagent containing a cholesterol oxidase, a cholesterol esterase, a peroxidase and the other of the coupler and the developer, wherein an aliphatic amine containing carboxyl group(s) or sulfonic acid group(s) are incorporated in at least one of the first reagent and the second reagent.

Namely, the present inventors have made extensive study for contriving a method for measuring an amount of LDL-cholesterol directly with the use of automatic analyzers without pre-treatment for separation of unnecessary lipoproteins other than LDL to find that LDL-cholesterol can selectively be measured without separation of unnecessary lipoproteins other than LDL by conducting measurement of cholesterol in the presence of an amphoteric surfactant and an aliphatic amine containing carboxyl group(s) or sulfonic acid group(s), based upon which the present invention has been completed.

DESCRIPTION OF THE PREFERRED EMBODIMENT

Figure 1:
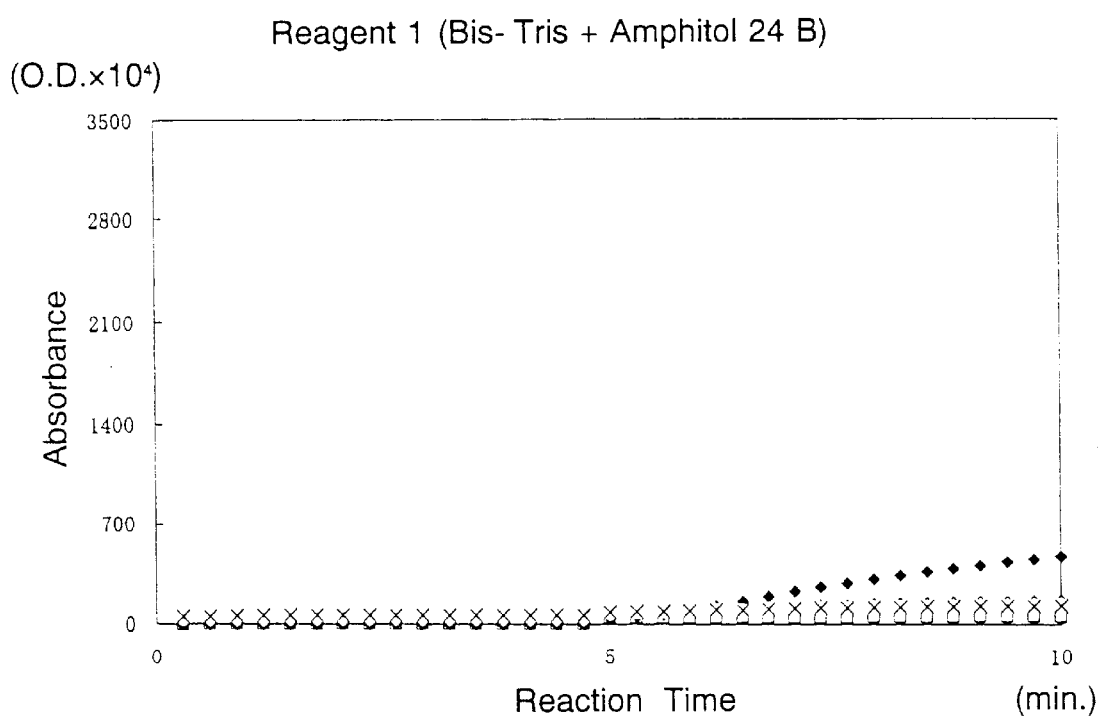
FIG. 1 Shows a reaction curve of various kind of samples containing various kinds of lipoproteins, which is obtained in Example 1.

The amphoteric surfactant used in the present invention is not specifically limited so far as it can prevent cholesterol in lipoproteins other than LDL from involving in the reaction for measuring an amount of cholesterol and is exemplified by betaine derivatives such as alkyl betaine derivatives (e.g. lauryl betaine, stearyl betaine, lauryl dimethylammonium betaine, coconut betaine, palm oil fatty acid amide propyl betaine, lauric acid amide propyl betaine, etc.), imidazolinium betaine derivatives (e.g. 2- alkyl-N-carboxymethyl-N-hydroxyethyl imidazolinium betaine such as 2-lauryl-N-carboxymethyl-N-hydroxyethyl imidazolinium betaine and 2-undecyl-N-carboxymethyl-N-hydroxyethyl imidazolinium betaine, 2-alkyl-N-carboxyethyl-N-hydroxyethyl imidazolinium betaine, etc.) and sulfo betaine derivatives (e.g. N-octyl-N,N-dimethyl-3-ammonio-1-propanesulfonic acid, N-decyl-N,N-dimethyl-3-ammonio-1-propanesulfonic acid, N-dodecyl-N,N-dimethyl-3-ammonio-1-propanesulfonic acid, N-tetradodecyl-N,N-dimethyl-3-ammonio-1-propanesulfonic acid, N-hexadecyl-N,N-dimethyl-3-ammonio-1 -propanesulfonic acid, etc.), amino carboxylic acid derivatives such as alkyl glycine, alkyl bis(aminoethyl) glycine, dioctyl polyaminoethyl glycine, N-alkyl polyaminoethyl glycine and β-alanin derivatives, imidazoline derivatives such as bis (2-undecyl-N-hydroxyethyl imidazoline) chloroacetic acid complex and alkyl imidazoline derivatives, amine oxide derivatives such as lauryl dimethylamine oxide, and the like.

Among these compounds, the amphoteric surfactant selected from the group consisting of lauryl betaine, palm oil fatty acid amide propyl betaine, lauric acid amide propyl betaine, 2-alkyl-N-carboxymethyl-N-hydroxyethyl imidazolinium betaine and 2-alkyl-N-carboxyethyl-N-hydroxyethyl imidazolinium betaine is more preferable.

The concentration of the amphoteric surfactant to be used is not specifically limited so far as it can prevent cholesterol in lipoproteins other than LDL from involving in the cholesterol measuring reaction, and generally it is added in such an amount that the final concentration in the reaction solution is 0.0001 to 10%(W/V), preferably 0.001 to 1%(W/V). The amphoteric surfactant may be used alone or in suitable combination of two or more thereof.

Additionally, when a nonionic surfactant is present in the method of the present invention, possibility of involving cholesterol in lipoproteins other than LDL in the cholesterol measuring reaction is increased, and therefore, it is preferable to conduct the method of the present invention in the absence of a nonionic surfactant.

The aliphatic amine containing carboxyl group(s) or sulfonic acid group(s) used in the present invention is not specifically limited so far as it prevents cholesterol in lipoproteins other than LDL from involving in the cholesterol measuring reaction, and includes amino acids, aminoethanesulfonic acid derivatives, aminopropanesulfonic acid derivatives and glycine derivatives, which have such properties as mentioned above.

The amino acids are exemplified specifically by alanine, glutamine and glutamic acid. The specific examples of the aminoethanesulfonic acid derivatives are N-(2-acetamido)-2-aminoethanesulfonic acid (ACES), N,N-bis(2-hydroxyethyl)-2-aminoethanesulfonic acid (BES), N-cyclohexyl-2-aminoethanesulfonic acid (CHES), 2-[4-(2-hydroxyethyl)-1-piperazinyl] ethanesulfonic acid (HEPES), 2-morpholinoethanesulfonic acid (MES), piperazine-1,4-bis (2-ethanesulfonic acid) (PIPES), N-tris(hydroxymethyl) methyl-2-aminoethanesulfonic acid (TES), etc., those of the aminopropanesulfonic acid derivatives are N-cyclohexyl-3-aminopropanesulfonic acid (CAPS), N-cyclohexyl-2-hydroxy-3-aminopropanesulfonic acid (CAPSO), 3-[N,N-bis(2-hydroxyethyl)amino]-2-hydroxy-propanesulfonic acid (DIPSO), 3-[4-(2-hydroxyethyl)-1-piperazinyl] propanesulfonic acid (EPPS), 2-hydroxy-3-[4-(2-hydroxyethyl)-1-piperazinyl] propanesulfonic acid (HEPPSO), 3-morpholinopropanesulfonic acid (MOPS), 2-hydroxy-3-morpholinopropanesulfonic acid (MOPSO), piperazine-1,4-bis (2-hydroxy-3-propanesulfonic acid) (POPSO), N-tris (hydroxymethyl)methyl-3-aminopropanesulfonic acid (TAPS), 2-hydroxy-N-tris(hydroxymethyl) methyl-3-aminopropanesulfonic acid (TAPSO), etc. and those of the glycine derivatives are N-(2-acetamido)iminodiacetic acid (ADA), N,N-bis (2-hydroxyethyl)glycine (Bicine), N-[tris (hydroxymethyl) methyl]glycine (Tricine), etc.

Among these compounds, the aliphatic amine containing carboxyl group(s) or sulfonic acid group(s) selected from the group consisting of 2-[4-(2-hydroxyethyl)-1-piperazinyl] ethanesulfonic acid (HEPES), 2-morpholinoethanesulfonic acid (MES), piperazine-1,4-bis(2-ethanesulfonic acid) (PIPES), 3-morpholinopropanesulfonic acid (MOPS) and N-(2-acetamido)iminodiacetic acid (ADA) is more preferable.

The concentration of the aliphatic amine containing carboxyl group(s) or sulfonic acid group(s) to be used is not specifically limited so far as it can prevent cholesterol in lipoprotein other than LDL from involving in the cholesterol measuring reaction, and generally such one that the final concentration in the reaction solution is 1 mM to 2M, preferably 10 mM to 1M, more preferably 100 to 700 mM, still more preferably 200 to 600 mM. This compound may be used alone or in suitable combination of two or more thereof.

The method of measuring an amount of the present invention can be conducted after a known method for measuring an amount of cholesterol, except for using together the above mentioned amphoteric surfactant and the aliphatic amine containing carboxyl group(s) or sulfonic acid group(s), and reagents to be used are also selected suitable from those in known methods.

Namely, LDL-cholesterol in a living sample such as plasma and serum is measured after a known cholesterol measuring method in the presence of the amphoteric surfactant and the aliphatic amine containing carboxyl group(s) or sulfonic acid group(s), whereby LDL-cholesterol in the living sample can specifically be measured.

Those known methods for measuring an amount of cholesterol includes, as preferable examples, an oxidizable colorimetric method with the use of enzymatic reaction, comprising digesting cholesterol ester in a sample into free cholesterol and a fatty acid by the act of a cholesterol esterase (CHE), then oxidizing the free cholesterol together with one originally existed by the act of a cholesterol oxidase (COD) to give cholest-4-en-3-on and hydrogen peroxide, allowing an oxidizable color forming reagent to cause dye by the act of thus produced hydrogen peroxide in the presence of a peroxidase (POD) and conducting calorimetric analysis of thus produced dye, and an ultraviolet (UV) spectrometric method, comprising digesting cholesterol ester in a sample into free cholesterol and a fatty acid by the act of a cholesterol esterase (CHE), reacting the free cholesterol together with one originally existed with NAD in the presence of a cholesterol dehydrogenase (CHD) and measuring the resulting NADH at 340 nm wave length.

The cholesterol oxidase used in the measuring method of the present invention is not specifically limited and all of those generally used in this field such as one originated from microorganisms belonging to the genus Nocardia, the genus Pseudomonas, etc. and one originated from internal organs of animals such as bovine pancreas, etc. can be used. An amount of the cholesterol oxidase to be used is generally 0.02 to 10 u/ml, preferably 0.1 to 2 u/ml as concentration in a reaction solution upon measurement of cholesterol.

The cholesterol esterase used in the measuring method of the present invention is not specifically limited and all of those generally used in this field such as one originated from microorganisms belonging to the genus Candida, the genus Pseudomonas, etc. and one originated from internal organs of animals such as bovine pancreas, etc. can be used. An amount of the cholesterol esterase to be used is generally 0.02 to 10 u/ml, preferably 0.1 to 2 u/ml as concentration in a reaction solution upon measurement of cholesterol.

The peroxidase used in the measuring method of the present invention is not specifically limited and all of those generally used in this field such as one originated from plants such as horseradish and radish, one originated from microorganisms such as fungi and yeast and one originated from leukocyte, thyroid gland, etc. of animals, etc. can be used. An amount of the peroxidase to be used is generally 0.01 to 50 u/ml, preferably 0.1 to 5 u/ml as concentration in a reaction solution upon measurement of cholesterol.

The oxidizable color forming reagent used in the measuring method of the present invention may be any of those which can react with hydrogen peroxide in the presence of POD to cause color, and is exemplified by a combination of a coupler such as 4-aminoantipyrine with a developer forming dye by oxidative condensation with the coupler, including a combination of 4-aminoantipyrine with a phenol compound, a naphthol compound or an aniline compound, a combination of 3-methyl-2-benzothiazolinone hydrazone with an aniline compound, etc., and by a color former which forms color by itself by oxidation, including 2,2'-azinobis (3-ethylbenzothiazoline-6-sulfonic acid), a triphenylmethane type leuco dye, a diphenylamine derivative, a benzidine derivative, a triallyl imidazole derivative, a leuco methylene blue derivative, an o-phenylenediamine derivative, etc.

Specific examples of the phenol compound as the developer are phenol, p-chlorophenol, 2,4-dichlorophenol, etc., those of the naphthol compound are 1-naphthol, 1-naphthol-2-sulfonic acid, 1-naphthol-2-carboxylic acid, etc. and those of the aniline compound are N,N-diethylaniline, N-ethyl-N-(β-hydroxyethyl)-m-toluidine, N-ethyl-N-(2-hydroxy-3-sulfopropyl)-3,5-dimethoxyaniline (DAOS), N-ethyl-N-(2-hydroxy-3-sulfopropyl)-3,5-dimethoxy-4-fluoroaniline (FDAOS), N-(2-hydroxy-3-sulfopropyl)-3,5-dimethoxyaniline (HDAOS), N-ethyl-N-(2-hydroxy-3-sulfopropyl)-m-toluidine (TOOS), N-ethyl-N-(3-methylphenyl)-N'-succinyl-ethylenediamine (EMSE), etc.

In case of using a combination of a coupler with a developer, an amount of the coupler to be used is not generalized because it is different according to the kind of the coupler and the developer to be combined, and it is usually selected from a range of generally 0.01 to 100 mM, preferably 0.1 to 10 mM, as concentration in the reaction solution upon measurement of cholesterol, and an amount in case of using 4-aminoantipyrine as the coupler is selected from a range of generally 0.01 to 50 mM, preferably 0.1 to 5 mM as concentration in the reaction solution upon measurement of cholesterol.

An amount of the developer to be used is not generalized because it is different according to the kind of the developer to be used and the coupler to be combined, and it is usually selected from a range of generally 0.01 to 50 mM, preferably 0.1 to 5 mM as concentration in the reaction solution upon measurement of cholesterol.

Specific examples of the triphenylmethane type leuco dye are leuco Malachite Green, bis(p-diethylaminophenyl)-2-sulfophenylmethane, bis(p-diethylaminophenyl)-3,4-disulfopropoxyphenylmethane disodium salt, etc., those of the diphenylamine derivatives are bis [4-di(2-butoxyethyl (amino-2-methylphenyl]amine, N,N-bis (4-diethylamino-2-methylphenyl)-N'-p-toluenesulfonyl urea, etc., those of leuco methylene blue derivative are 10-(carboxymethylaminocarbonyl)-3,7-bis (dimethylamino) phenothiazin sodium salt, 10-[3-(methoxycarbonylaminomethyl) phenylmethylaminocarbonyl]-3,7-bis(dimethylamino) phenothiazin, etc., those of the benzidine derivative are benzidine, o-tolidine, o-dianisidine, 3,3'-diaminobenzidine, 3,3',5,5'-tetraaminobenzidine, etc. and those of the triallylimidazole are 2-(4-carboxyphenyl)-3-N-methylcarbamoyl-4,5-bis (4-diethylaminophenyl)imidazole, 2-(3-methoxy-4-diethylaminophenyl)-3-N-methylcarbamoyl-4,5-bis(2-methyl-4-diethylaminophenyl) imidazole, etc.

An amount of the color former to be used is selected from a range which has been generally used in this field.

The reagent for measuring an amount of LDL-cholesterol of the present invention is used for measuring LDL-cholesterol in a living sample such as plasma and serum, and it is prepared in such a way that there are incorporated, in addition to the amphoteric surfactant and the aliphatic amine containing carboxyl group(s) or sulfonic acid group(s), the reagents for measuring an amount of cholesterol used in known methods for measuring an amount of cholesterol as mentioned above, such as reagents used in an oxidizable colorimetric method including COD, CHE, POD, an oxidizable color forming reagent, a buffering agent, etc. and reagents used in UV spectrometric method including CHE, CHD, NAD, a buffering agent, etc. in such an amount as having been used in this field, and preferable embodiments and preferable amounts are as mentioned above.

The reagent for measuring an amount of LDL-cholesterol of the present invention can be prepared as one-reagent system or two- or more-reagent system, and there is no specific limitation in this regard. The amphoteric surfactant and the aliphatic amine containing carboxyl group(s) or sulfonic acid group(s) may be incorporated at least in any of the reagents in case of two- or more-reagent system. The cholesterol oxidase, the cholesterol esterase and other enzymes may also be incorporated in any of the reagents.

In the reagent for measuring an amount of LDL-cholesterol of the present invention, there may be incorporated an ionic compound including anionic compounds such as a polyanion (for example, dextran sulfate, heparin, heparan sulfate, phosphotungstic acid, etc.). They may be used alone or in combination thereof. They may be used in combination with a cation such as $Mg^{2+}$, $Mn^{2+}$ and $Ca^{2+}$ (or a metal salt generating the cation). Concentration of the ionic compound to be used is not limited and generally selected from a range of 0.01 to 10% (w/v) as one in the reaction solution.

In the reagent for measuring an amount of LDL-cholesterol of the present invention, there may be incorporated one or more of polyclonal antibody or monoclonal antibody in order to prevent cholesterol in lipoproteins other than LDL from involving in the cholesterol measuring reaction.

The antibody used for this purpose includes anti-apolipoprotein A antibody, anti-apolipoprotein C antibody, anti-apolipoprotein E antibody, anti-α lipoprotein antibody, etc. so far as it is one capable of preventing cholesterol in lipoproteins other than LDL from involving in the cholesterol measuring reaction, and the antibody is added to the reaction system in such an amount as the final concentration in the reaction solution being generally 0.001 to 10 mgAb/ml, preferably 0.01 to 1 mgAb/ml.

The method for measuring an amount of LDL-cholesterol of the present invention can be conducted by two-reagent method.

In this method, each of the amphoteric surfactant and the aliphatic amine containing carboxyl group(s) or sulfonic acid group(s) may be incorporated in at least one of the first reagent and the second reagent, and each of the coupler, the developer and the peroxidase may be incorporated at least one of the first reagent and the second reagent.

In the first and second reagents, the ingredients are dissolved in an aqueous medium.

The aqueous medium includes water and a buffer solution. Generally, a buffer solution is preferable.

As the first reagent, use may be made of one containing only the aqueous medium without any ingredient.

When the aqueous medium of the first reagent is water, it is preferable that the aqueous medium of the second reagent is a buffer solution.

When a buffer solution is used as the aqueous medium, it is preferable to incorporate a buffer solution into in either of the first reagent or the second reagent whichever contains no aliphatic amine containing carboxyl group(s) or sulfonic groups(s).

The buffering agent used in the measuring method of the present Invention is not specifically limited and all of those generally used in this field are used, so far as having buffering ability to keep pH 5 to 11 and not inhibiting the measuring reaction of the LDL-cholesterol.

The typical examples thereof are tris(hydroxymethyl) aminomethane Good's buffering agent, phosphates, borates, etc. The concentration of the buffering agent to be used is not specifically limited and is generally selected from a range of 1 mM to 2M, preferably 10 mM to 1M, and a pH range to be kept is generally selected from a range of 5 to 11, preferably 6 to 8, more preferably around 7.

One of the preferable embodiments of this measuring method is mentioned below.

A living sample such as plasma and serum is mixed with a first reagent comprising an aqueous medium, a coupler, an amphoteric surfactant and an aliphatic amine containing carboxyl group(s) or sulfonic acid group(s) and, if necessary, an ionic compound, a cation, an antibody etc., followed by allowing a reaction to take place at 2° to 40° C. for 1 to 30 minutes, and an absorbance (OD1) of a resulting reaction solution is measured. Then, the resulting reaction solution is mixed with a second reagent solution containing a cholesterol esterase, a cholesterol oxidase, a peroxidase, a developer and an aliphatic amine containing carboxyl group(s) or sulfonic acid group(s), followed by allowing a reaction to take place at 2° to 40° C. for 1 to 60 minutes and an absorbance (OD2) is measured. A value derived from the OD1 (for example, a value obtained by multiplying OD1 by a correction coefficient is subtracted from the OD2 to give an absorbance (OD3). Thus obtained the OD3 is applied to a calibration curve showing a relation between an amount of solution containing a cholesterol esterase, a cholesterol oxidase, a peroxidase, an oxidizable color forming reagent (or a coupler and a developer), an amphoteric surfactant and an aliphatic amine containing carboxyl group(s) or sulfonic acid group(s) and, if necessary, an ionic compound, a cation, an antibody etc., followed by allowing a reaction to take place at 2° to 40° C. for 1 to 30 minutes and an absorbance (OD1) is measured. The same procedure as above with the use of the same reagent above except for using physiological saline in place of the living sample and a blank value (ODBl) is measured. Then the ODBl is subtracted from OD1' to give an absorbance (OD2'), and thus obtained OD2' is applied to a calibration curve showing a relation between an amount of cholesterol and OD2', which is previously prepared by conducting the above process with the use of a standard specimen containing a predetermined amount of cholesterol, whereby the amount of LDL-cholesterol in the living sample can be detected.

Additionally a buffering agent mentioned before may be incorporated in the reagent solution.

The kit for measuring an amount of LDL-cholesterol of the present invention is used for measuring an amount of LDL-cholesterol in a living sample such as plasma and serum, and comprises a first reagent containing one of a coupler and a developer and a second reagent containing a cholesterol oxidase, a cholesterol esterase, a peroxidase and the other of the coupler and the developer, wherein each of an amphoteric surfactant and an aliphatic amine containing carboxyl group(s) or sulfonic acid group(s) are incorporated in at least one of the first reagent and the second reagent, and preferable embodiments of each ingredient and specific examples are as mentioned above. The kit may be in combination with a standard specimen.

An amphoteric surfactant may deactivate cholesterol esterase, and thus they are preferably separated from each other. Under the situation, the following is more preferable combination of the kit for measuring an amount of LDL-cholesterol of the present invention, considering storage stability.

The kit is one comprising a first reagent containing an amphoteric surfactant and one of a coupler and a developer and a second reagent containing a cholesterol oxidase, a cholesterol esterase, a peroxidase and the other of the coupler and the developer, wherein an aliphatic amine containing carboxyl group(s) or sulfonic acid group(s) are incorporated in at least one of the first reagent and the second reagent. The kit may be in combination with a standard specimen.

The characteristic of the method and the kit for measuring an amount of LDL-cholesterol of the present invention can cause measurement of cholesterol in the presence of an amphoteric surfactant and an aliphatic amine containing carboxyl group(s) or sulfonic acid group(s), and thus, cholesterols in lipoproteins other than LDL, such as not only HDL but also VLDL and chylomicrons are substantially not involved in a reaction and a reaction specifically with LDL-cholesterol is allowed to take place. Therefore, measuring an amount of LDL-cholesterol by end point assay, which has been difficult to conduct by known methods, can be conducted. The standard specimen is not necessary to be a standard solution prepared by using pure cholesterol. That is, for example, in the present invention, the standard serum prepared by using human or animals sera can be used as the standard specimen.

In the following, the present invention is explained further in detail referring to examples and reference examples, and it is not limited thereto in any event.

EXAMPLE 1

Reactivities of lipoproteins fractionated by ultra-centrifugation were compared by the method for measuring an amount of the present invention with the use of an automatic analyzer Hitachi 7170 [manufactured and sold by Hitachi, Ltd.].

(Samples)

HDL fraction(64.9 mg/dl), LDL fraction(148.2 mg/dl), VLDL fraction(76.3 mg/dl) or CM fraction(28.4 mg/dl) obtained from serum after known ultra-centrifugation method were used as sample.

(Reagents)

Reagent 1

R-I; R-1 was 200 mM bis(2-hydroxyethyl)iminotris (hydroxymethyl) methane (Bis-Tris) buffer solution (pH 7.0) containing 1 mM of 4-aminoantipyrine.

R-2: R-2 was 200 mM bis(2-hydroxyethyl)iminotris (hydroxymethyl) methane (Bis-Tris) buffer solution (pH 7.0) containing 2 u/ml of cholesterol oxidase (CHO"Amano"VW; Product Name of Amano Pharmaceutical Co., Ltd.), 2 u/ml of cholesterol esterase (Product Code; T-18, product of Asahi Chemical Industry Co., Ltd.), 1 u/ml of peroxidase (Product Code; PEO-302, product of Toyobo Co., Ltd.), 1 mM of N-ethyl-N-(2-hydroxy-3-sulfopropyl)-3,5-dimethoxyaniline Na salt (DAOS) and 0.08%(W/V) of Amphitol 24 B (Product Name of Kao Corp., coconut betaine)

Reagent 2

R-1; R-1 was 200 mM piperazine-1,4-bis(2-ethanesulfonic acid (PIPES) buffer solution (pH 7.0) containing 1 mM of 4-aminoantipyrine.

R-2: R-2 was 200 mM piperazine-1,4-bis(2-ethanesulfonic acid ) (PIPES) buffer solution (pH 7.0) containing 2 u/ml of cholesterol oxidase (CHO"Amano"VW; Product Name of Amano Pharmaceutical Co., Ltd.), 2 u/ml of cholesterol esterase (Product Code; T-18, product of Asahi Chemical Industry Co., Ltd.), 1 u/ml of peroxidase (Product Code; PEO-302, product of Toyobo Co., Ltd.), 1 mM of N-ethyl-N-(2-hydroxy-3-sulfopropyl)-3,5-dimethoxyaniline Na salt (DAOS) and 0.08%(W/V) of Amphitol 24 B (Product Name of Kao Corp., coconut betaine).

Reagent 3

R-1; R-1 was 200 mM N-(2-acetamido)iminodiacetic acid (ADA) buffer solution (pH 7,0) containing 1 mM of 4-aminoantipyrine.

R-2; R-2 was 200 mM N-(2-acetamido)iminodiacetic acid (ADA) buffer solution (pH 7,0) containing 2 u/ml of cholesterol oxidase (CHO"Amano"VW; Product Name of Amano Pharmaceutical Co., Ltd.), 2 u/ml of cholesterol esterase (Product Code; T-18, product of Asahi Chemical Industry Co., Ltd.), 1 u/ml of peroxidase (Product Code; PEO-302, product of Toyobo Co., Ltd.), 1 mM of N-ethyl-N-(2-hydroxy-3-sulfopropyl)-3,5-dimethoxyaniline Na salt (DAOS) and 0.1%(W/V) of Softazoline LPB-R (Product Name of Kawaken Fine Chemicals Co., Ltd., lauric acid amide propyl betaine).

(Measuring conditions)

Measurement was conducted with setting forth the measurement parameters as follows.

measuring method; 2 point end [16]–[34]

Sample amount; 3 µl

R-1; 270 µl

R-2; 90 µl

Measuring wave length; 700/600 nm

Measuring temperature; 37° C.

(Result)

Figure 2:
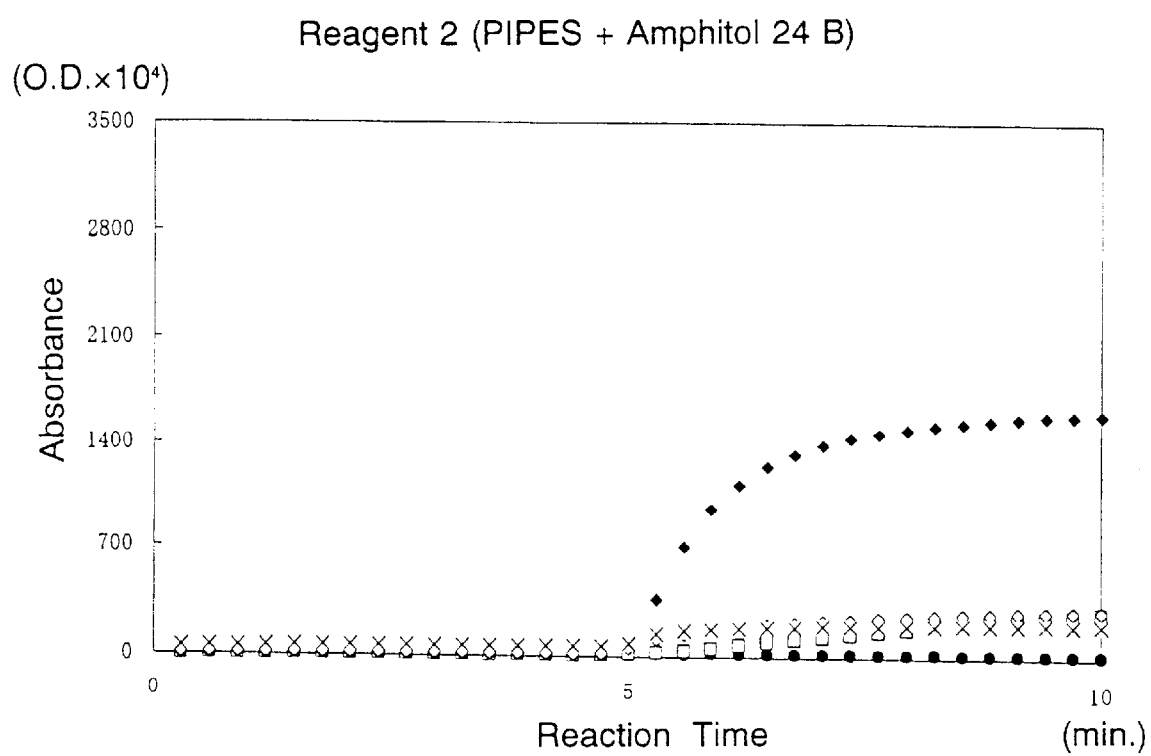
FIG. 2 Shows a reaction curve of various kind of samples containing various kinds of lipoproteins, which is obtained in Example 1.
Figure 3:
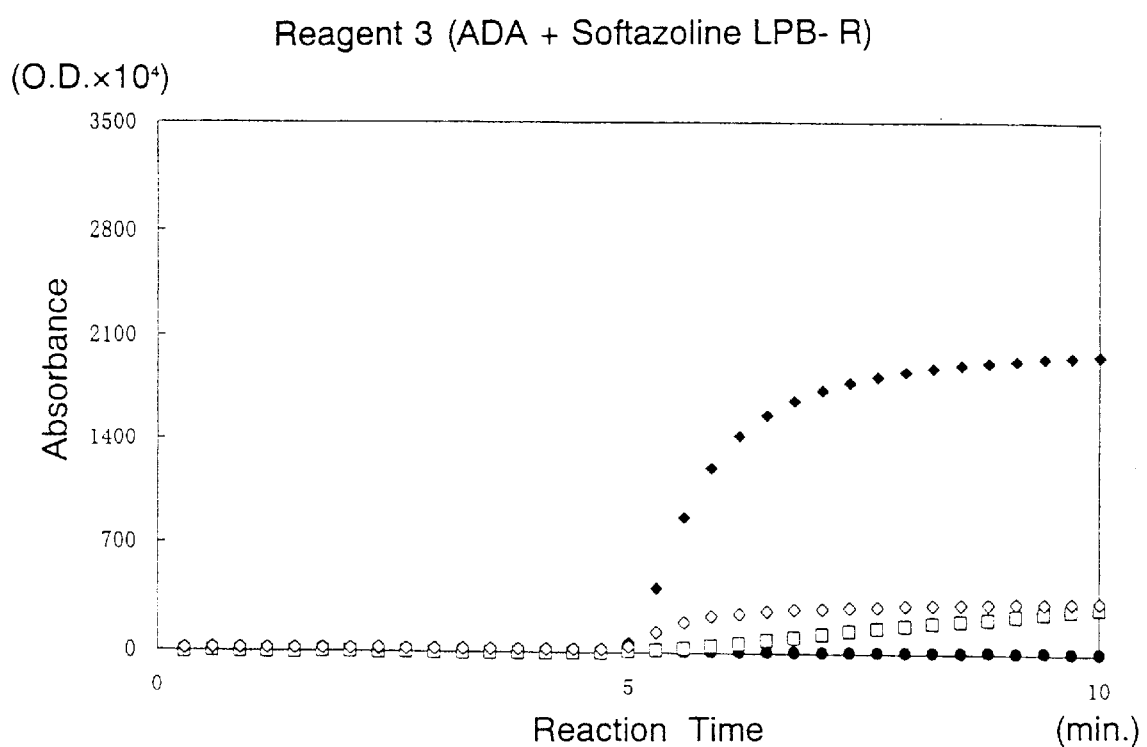
FIG. 3 Shows a reaction curve of various kind of samples containing various kinds of lipoproteins, which is obtained in Example 1.
Figure 4:
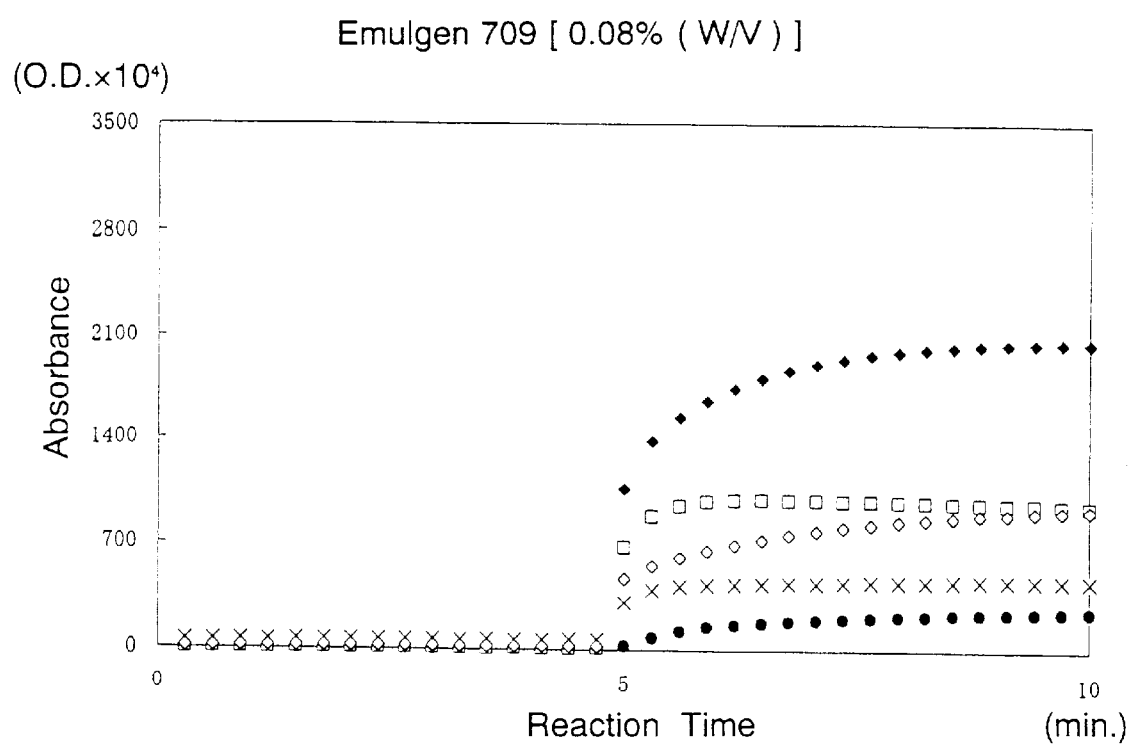
FIG. 4 Shows a reaction curve of various kind of samples containing various kinds of lipoproteins, which is obtained in Example 2.
Figure 5:
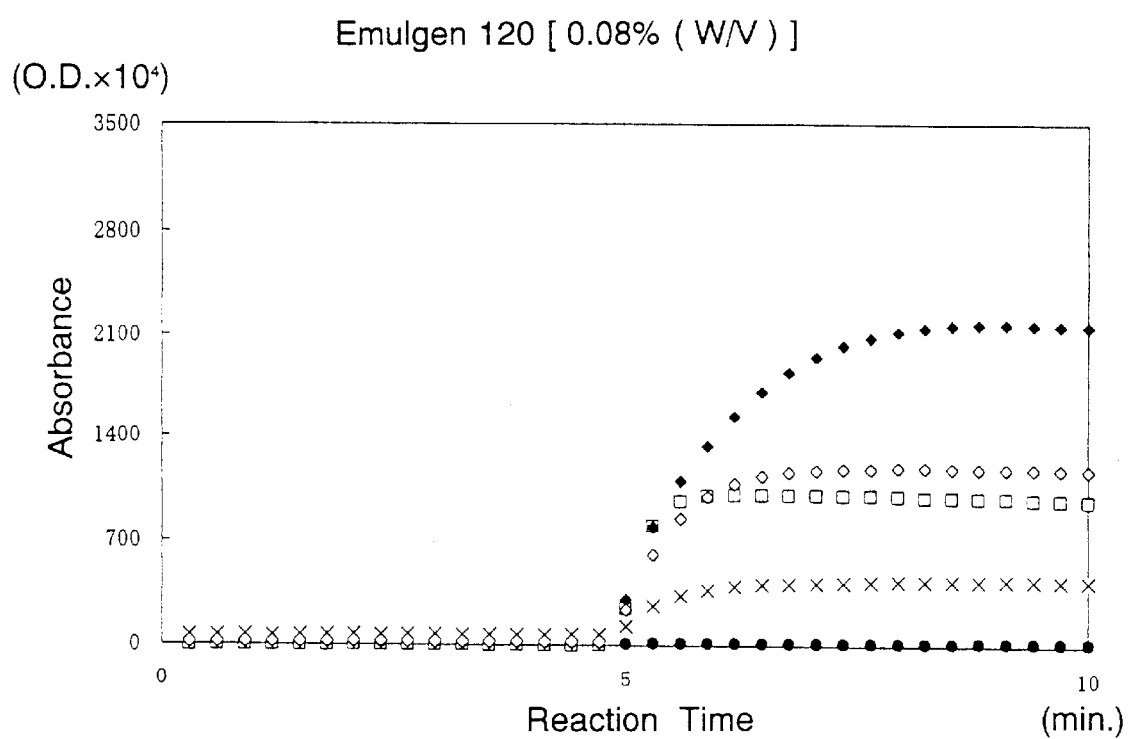
FIG. 5 Shows a reaction curve of various kind of samples containing various kinds of lipoproteins, which is obtained in Example 2.
Figure 6:
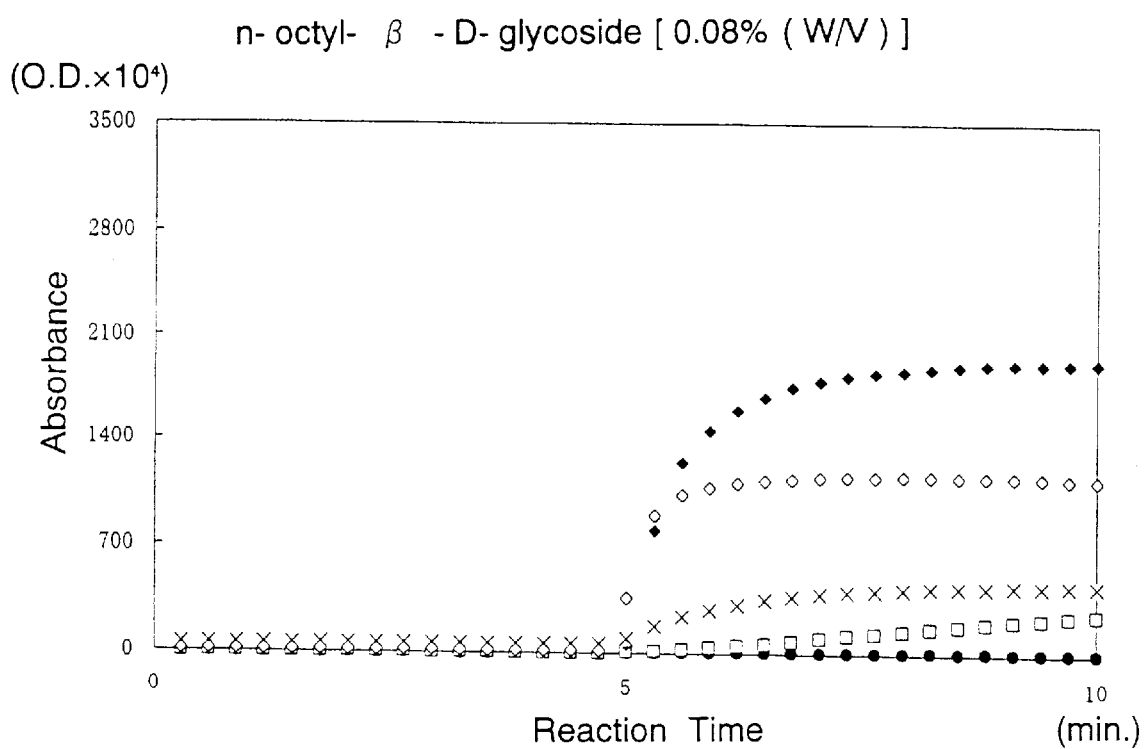
FIG. 6 Shows a reaction curve of various kind of samples containing various kinds of lipoproteins, which is obtained in Example 2.
Figure 7:
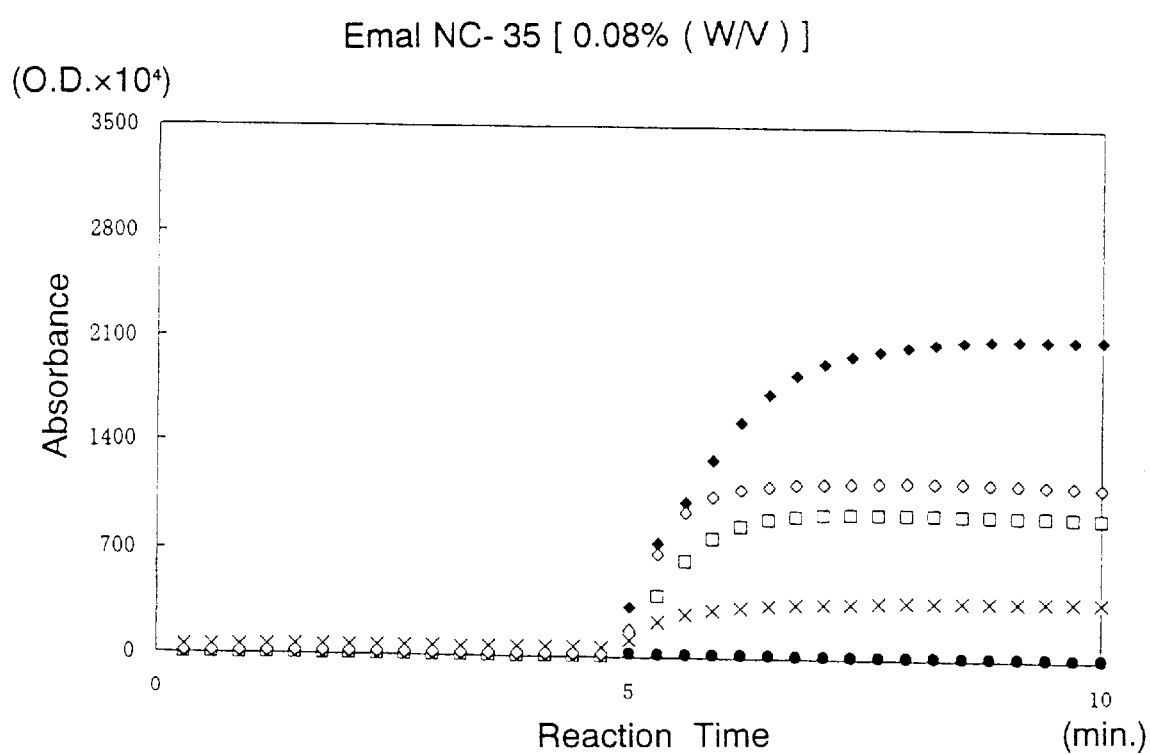
FIG. 7 Shows a reaction curve of various kind of samples containing various kinds of lipoproteins, which is obtained in Example 2.
Figure 8:
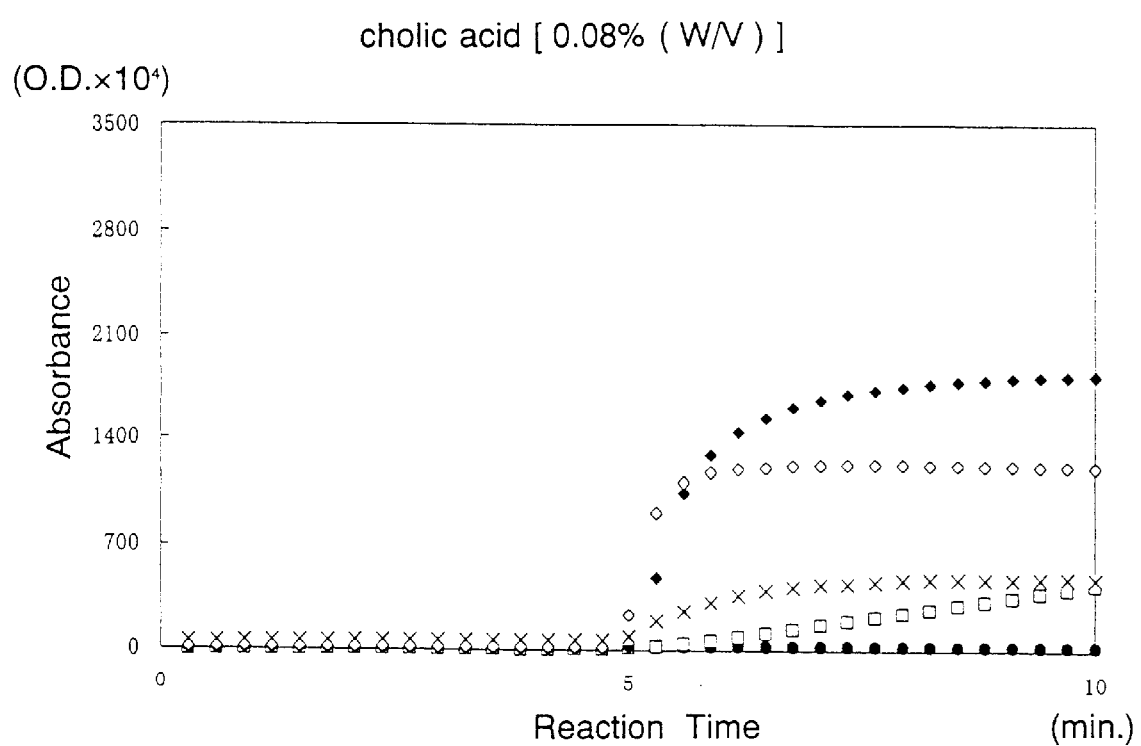
FIG. 8 Shows a reaction curve of various kind of samples containing various kinds of lipoproteins, which is obtained in Example 2.
Figure 9:
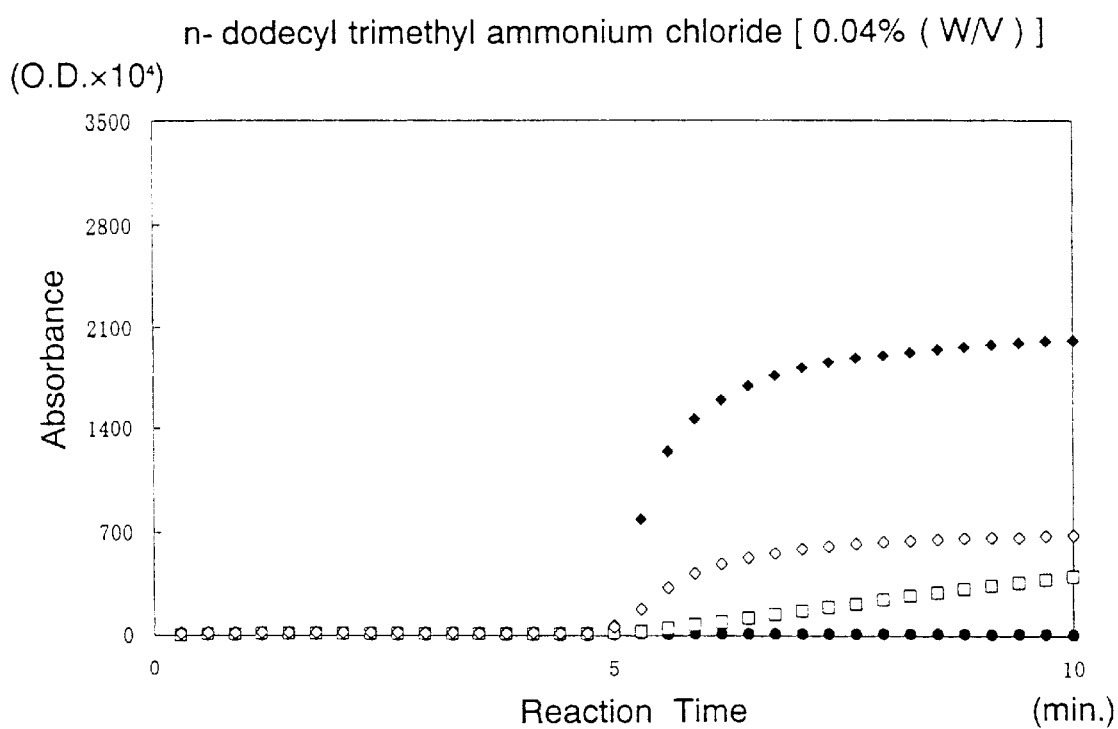
FIG. 9 Shows a reaction curve of various kind of samples containing various kinds of lipoproteins, which is obtained in Example 2.
Figure 10:
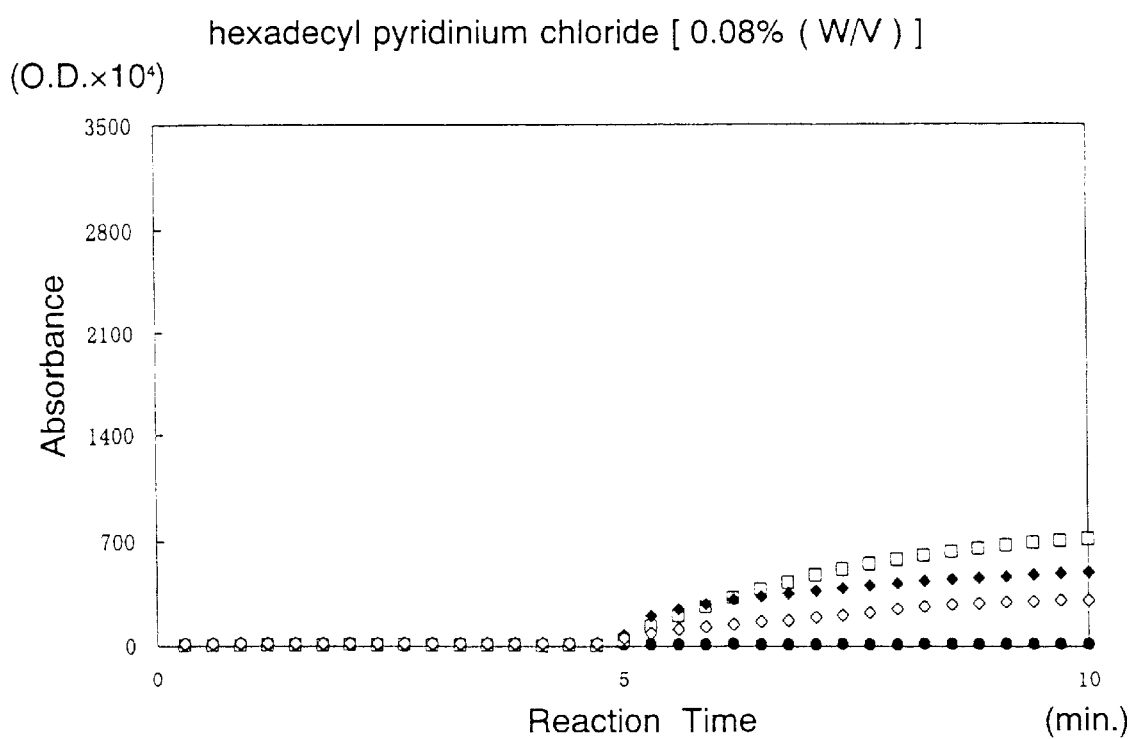
FIG. 10 Shows a reaction curve of various kind of samples containing various kinds of lipoproteins, which is obtained in Example 2.
Figure 11:
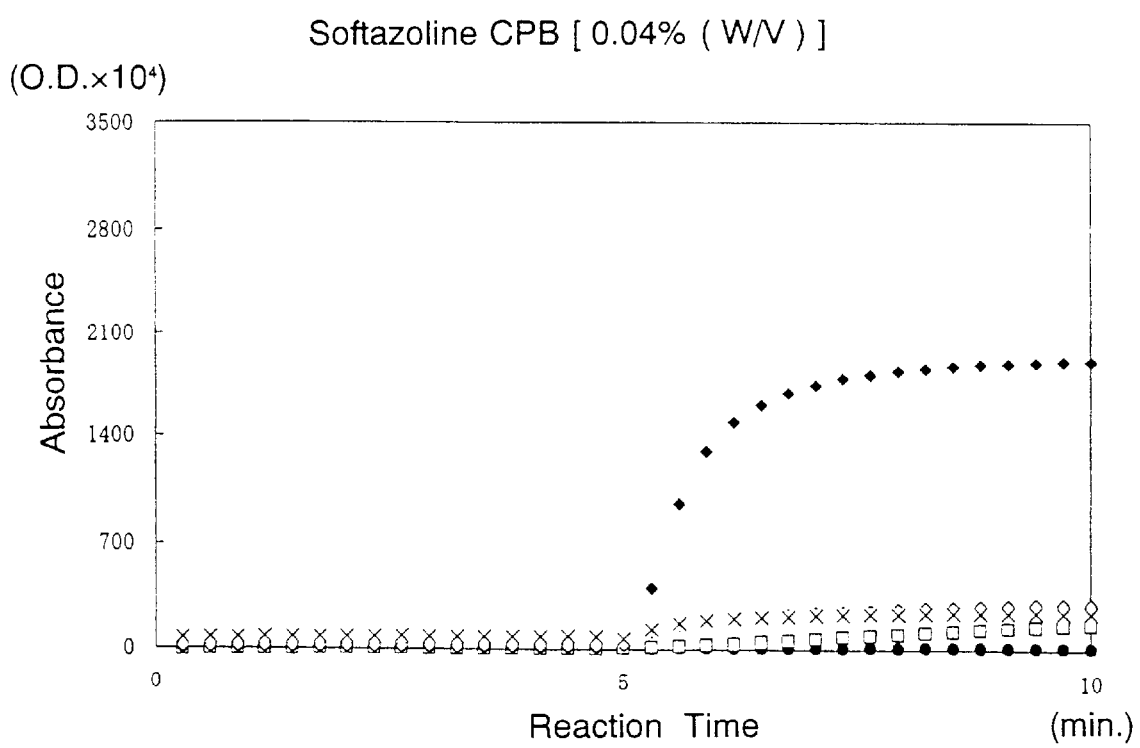
FIG. 11 Shows a reaction curve of various kind of samples containing various kinds of lipoproteins, which is obtained in Example 2.
Figure 12:
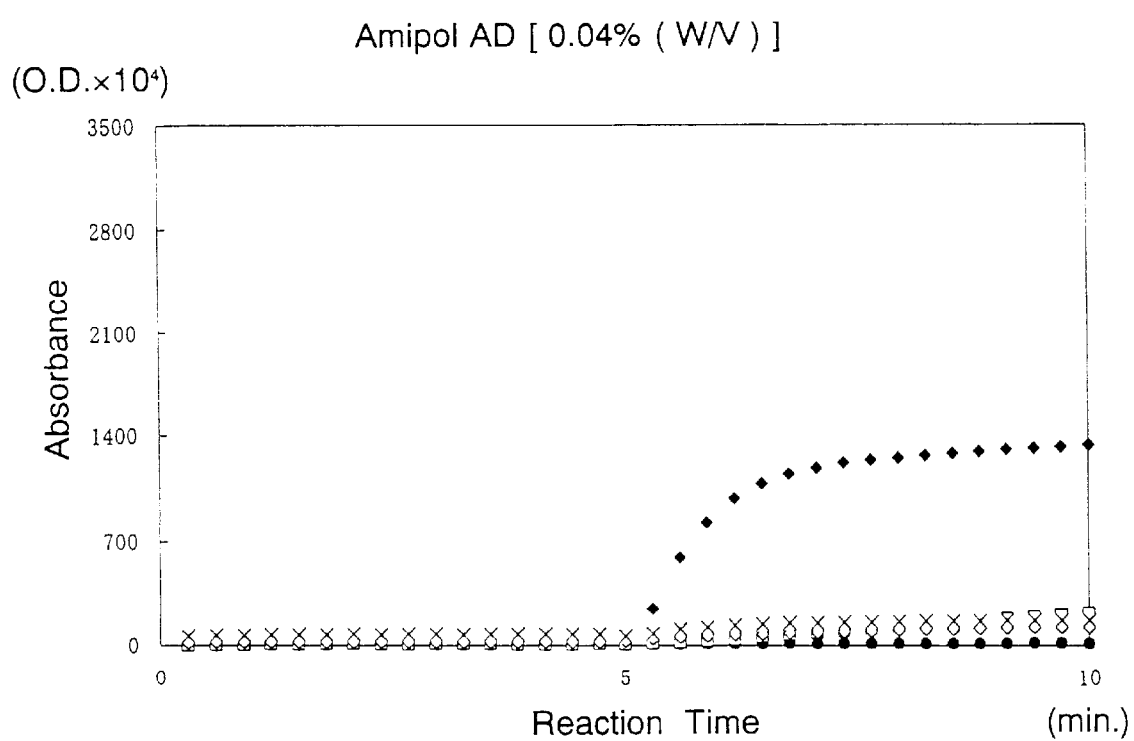
FIG. 12 Shows a reaction curve of various kind of samples containing various kinds of lipoproteins, which is obtained in Example 2.
Figure 13:
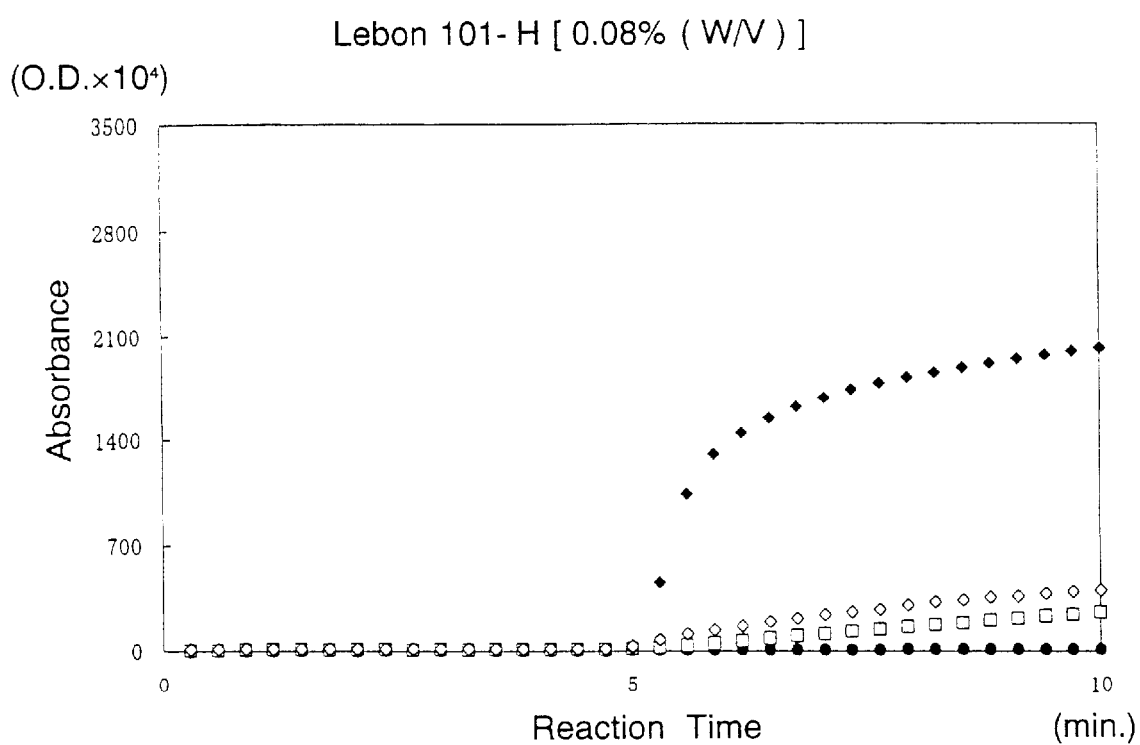
FIG. 13 Shows a reaction curve of various kind of samples containing various kinds of lipoproteins, which is obtained in Example 2.
Figure 14:
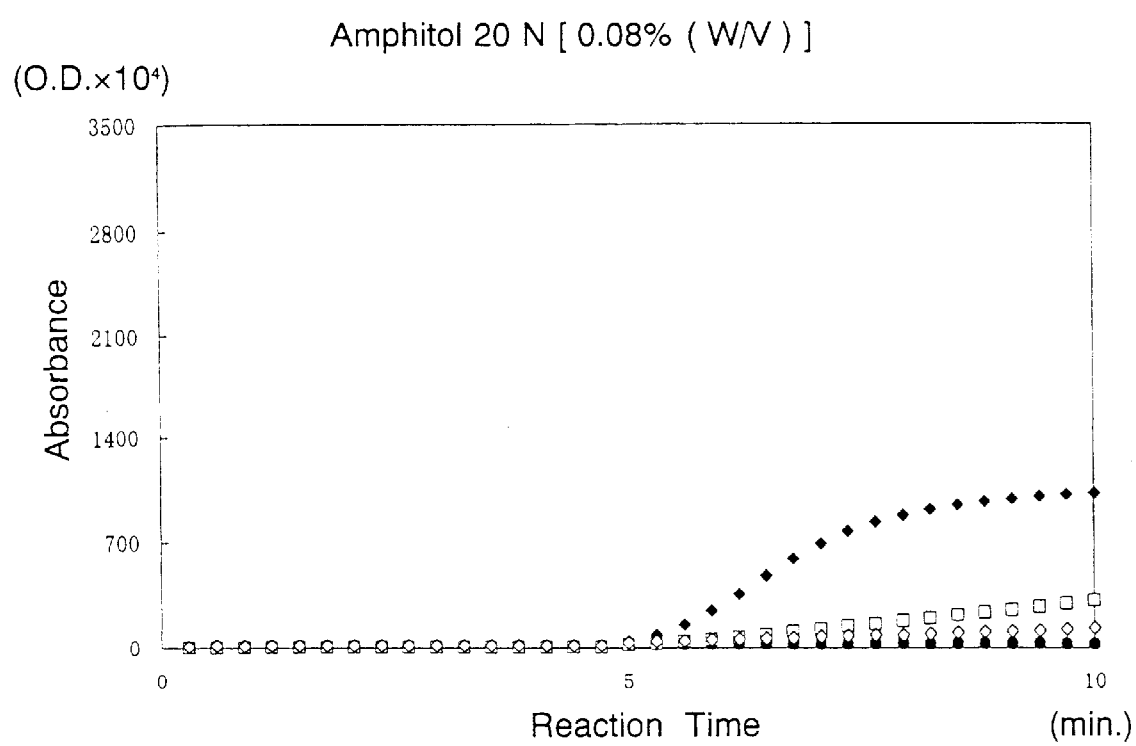
FIG. 14 Shows a reaction curve of various kind of samples containing various kinds of lipoproteins, which is obtained in Example 2.

The measurement result using the reagent 1, that using the reagent 2 and that using the reagent 3 are shown in FIG. 1, FIG. 2 and FIG. 3, respectively.

In FIG. 1 to 3, □ shows the result obtained in a sample containing HDL, ♦ shows the result obtained in a sample containing LDL, ◊ shows the result obtained in a sample containing VLDL, x shows the result obtained in a sample containing CM and ● shows the result obtained in a sample containing no lipoprotein, respectively.

From the result of measurement in FIG. 1, it can be understood that the reagent 1 containing Amphitol 24 B as an amphoteric surfactant, but no aliphatic amine containing carboxyl group(s) or sulfonic acid group(s) is almost not reacted with cholesterol in lipoproteins.

On the other hand, from the result of measurement in FIG. 2, it can be understood that cholesterol in LDL can specifically be measured by measuring an amount of cholesterol in lipoproteins in the presence of Amphitol 24 B and piperazine-1,4-bis (2-ethanesulfonic acid ) (PIPES) as an aliphatic amine containing sulfonic acid group. Similarly from the result of measurement in FIG. 3, it can be understood that cholesterol in LDL can specifically be measured by measuring an amount of cholesterol in lipoproteins in the presence of Softazoline LPB-R and N-(2-acetamide) iminodiacetic acid (ADA) as an aliphatic amine containing carboxyl group.

From the above, it is understood that cholesterol in LDL can specifically be measured by measuring an amount of cholesterol in lipoproteins in the presence of an amphoteric surfactant and an aliphatic amine containing carboxyl group(s) or sulfonic acid group(s).

EXAMPLE 2

(Sample) The same as Example 1

(Reagent)

R-1; R-1 was 200 mM 2-morpholinoethanesulfonic acid (MES) buffer solution (pH 7.0) containing 1 mM of 4-aminoantipyrine.

R-2: R-2 was 200 mM 2-morpholinoethanesulfonic acid (MES) buffer solution (pH 7.0) containing 2 u/ml of cholesterol oxidase (CHO"Amano"VW; Product Name of Amano Pharmaceutical Co., Ltd.), 2 u/ml of cholesterol esterase (Product Code; T-18, product of Asahi Chemical Industry Co., Ltd.), 1 u/ml of peroxidase (Product Code; PEO-302, product of Toyobo Co., Ltd.), 1 mM of N-ethyl-N-(2-hydroxy-3-sulfopropyl)-3,5-dimethoxyaniline Na salt (DAOS) and a predetermined concentration of a surfactant listed the following table 1.

TABLE 1

| | surfactant | | concentration in R-2 |
|---|---|---|---|
| nonionic surfactant | Emulgen 709 [Product Name of Kao Corp.] (polyoxyethylene higher alcohol ether) | | 0.08% (W/V) |
| | Emulgen 120 [Product Name of Kao Corp.] (polyoxyethylene lauryl ether) | | 0.08% (W/V) |
| | n-octyl-β-D-glycoside [Product of Dojin Kagaku Kenkyusho] | | 0.08% (W/V) |
| anionic surfactant | Emal NC-35 [Product Name of Kao Corp.] (polyoxyethylene alkylphenyl ether sodium sulfate) | | 0.08% (W/V) |
| | cholic acid [Product of Wako Pure Chem. Ind. Ltd.] | | 0.08% (W/V) |
| cationic surfactant | n-dodecyl trimethyl ammonium chloride [Product of Tokyo Kasei Kogyo] | | 0.04% (W/V) |
| | hexadecyl pyridinium chloride [Product of Wako Pure Chem. Ind. Ltd.] | | 0.08% (W/V) |
| amphoteric surfactant | Softazoline CPB [Product Name of Kawaken Fine Chemicals Co., Ltd.] (palm oil fatty acid amide propyl betaine, betaine derv.) | | 0.04% (W/V) |
| | Amipol AD [Product Name of Nikka Kayaku] (amino carboxylic acid derv.) | | 0.04% (W/V) |
| | Lebon 101-H [Product Name of Sanyo Chem. Ind. Ltd.] (imidazoline deriv.) | | 0.08% (W/V) |
| | Amphitol 20 N [Product Name of Kao Corp.] (lauryl dimethylamine oxide, amine oxide deriv.) | | 0.08% (W/V) |

(Measuring conditions)

The same as Example 1.

(Result)

The result of measurement using R-2 containing Emulgen 709 as a surfactant, the result of measurement using R-2 containing Emulgen 120 as a surfactant, the result of measurement using R-2 containing n-octyl-β-D-glycoside as a surfactant, the result of measurement using R-2 containing Emal NC-35 as a surfactant, the result of measurement using R-2 containing cholic acid as a surfactant, the result of measurement using R-2 containing n-dodecyl trimethyl ammonium chloride as a surfactant, the result of measurement using R-2 containing hexadecyl pyridinium chloride as a surfactant, the result of measurement using R-2 containing Softazoline CPB as a surfactant, the result of measurement using R-2 containing Amipol AD as a surfactant, the result of measurement using R-2 containing Lebon 101-H as a surfactant and the result of measurement using R-2 containing Amphitol 20 N as a surfactant are shown in FIG. 4, FIG. 5, FIG. 6, FIG. 7, FIG. 8, FIG. 9, FIG. 10, FIG. 11, FIG. 12, FIG. 13 and FIG. 14, respectively.

In FIG. 4 to 13, □ shows the result obtained in a sample containing HDL, ♦ shows the result obtained in a sample containing LDL, ◊ shows the result obtained in a sample containing VLDL, x showed the result obtained in a sample containing CM and ● shows the result obtained in a sample containing no lipoprotein.

As clear from the measurement results in FIG. 4 to 10, it is understood that cholesterols contained in lipoproteins other than LDL are also involved in a reaction when the reagent R-2 containing a nonionic surfactant, an anionic surfactant or a cationic surfactant is used.

On the other hand, it is understood from the measurement results in FIG. 11 to 14 that cholesterol in LDL can specifically be measured when the reagent R-2 containing an amphoteric surfactant is used.

EXAMPLE 3

(Samples)

HDL fraction(63.1 mg/dl), LDL fraction(138.1 mg/dl), VLDL fraction(77.3 mg/dl) or CM fraction(35.0 mg/dl) obtained from serum after known ultra-centrifugation method were used as sample.

(Reagent)

R-1; R-1 was 100 mM bis(2-hydroxyethyl)iminotris (hydroxymethyl) methane (Bis-Tris) buffer solution (pH 7.0) containing 400 mM of glutamic acid and 0.6 mM of N-(2-hydroxy-3-sulfopropyl)-3,5-dimethoxyaniline (HDAOS).

R-2: R-2 was 100 mM bis(2-hydroxyethyl)iminotris (hydroxymethyl) methane (Bis-Tris) buffer solution (pH 7.0) containing 2 u/ml of cholesterol oxidase (CHO"Amano"VW; Product Name of Amano Pharmaceutical Co., Ltd.), 1.6 u/ml of cholesterol esterase (Product Code; T-18, product of Asahi Chemical Industry Co., Ltd.), 6 u/ml of peroxidase (Product Code; PEO-302, product of Toyobo Co., Ltd.), 3 mM of 4-aminoantipyrine and 0.1% (W/V) of Softazoline CL (Product Name of Kawaken Fine Chemicals Co., Ltd., 2-alkyl-N-carboxymethyl-N-hydroxymethyl imidazolinium betaine)

(Measuring conditions)

The same as Example 1.

(Result)

Figure 15:
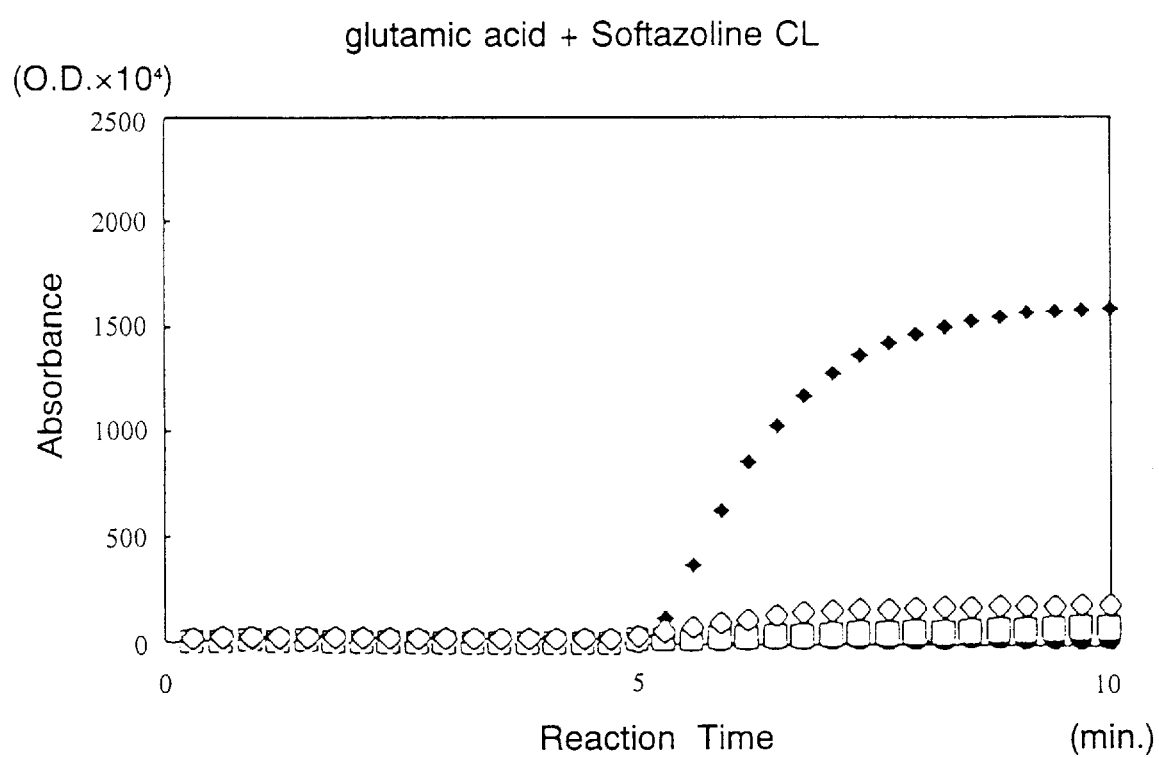
FIG. 15 Shows a reaction curve of various kind of samples containing various kinds of lipoproteins, which is obtained in Example 3.

The result of measurement is shown in FIG. 15.

In FIG. 15, □ shows the result obtained in a sample containing HDL, ◆ shows the result obtained in a sample containing LDL, ◇ shows the result obtained in a sample containing VLDL, ○ showed the result obtained in a sample containing CM and ● shows the result obtained in a sample containing no lipoprotein.

From the result of measurement in FIG. 15, it is understood that cholesterol in LDL can specifically be measured by measuring an amount of cholesterol in lipoproteins in the presence of Softazoline CL as an amphoteric surfactant and glutamic acid as an amino acid.

EXAMPLE 4

(Sample) The same as Example 3

(Reagent)

R-1; R-1 was 400 mM piperazine-1,4-bis(2-ethanesulfonic acid) (PIPES) buffer solution (pH 7.0) containing 0.6 mM of N-(2-hydroxy-3-sulfopropyl)-3,5-dimethoxyaniline (HDAOS).

R-2: R-2 was 400 mM piperazine-1,4-bis(2-ethanesulfonic acid) (PIPES) buffer solution (pH 7.0) containing 2 u/ml of cholesterol oxidase (CHO"Amano"VW; Product Name of Amano Pharmaceutical Co., Ltd.), 1.6 u/ml of cholesterol esterase (Product Code; T-18, product of Asahi Chemical Industry Co., Ltd.), 6 u/ml of peroxidase (Product Code; PEO-302, product of Toyobo Co., Ltd.), 3 mM of 4-aminoantipyrine and 0.08%(W/V) of an amphoteric surfactant listed the following table 2.

TABLE 2

| amphoteric surfactant |
| --- |
| Softazoline CL [Product Name of kawaken Fine Chemicals Co., Ltd.] (2-alkyl-N-carboxymethyl-N-hydroxymethyl imidazolinium betaine) |
| Softazoline NS [Product Name of Kawaken Fine Chemicals Co., Ltd.] (palm oil-alkyl-N-carboxymethyl-N-hydroxyethyl imidazolinium betaine) (palm oil deriv.) |
| Enagicol C-40H [Product Name of Lion Corp.] (2-alkyl-N-carboxymethyl-hydroxyethyl imidazolinium betaine) |

(Measuring conditions)

The same as Example 1

(Result)

Figure 16:
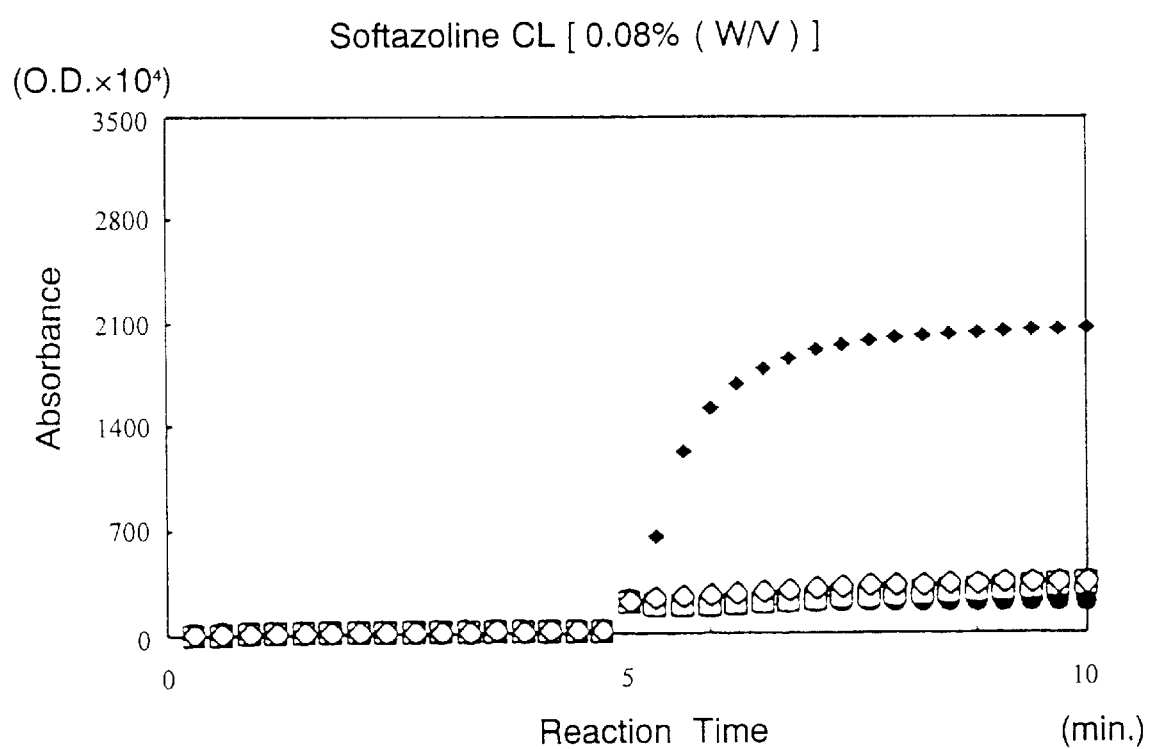
FIG. 16 Shows a reaction curve of various kind of samples containing various kinds of lipoproteins, which is obtained in Example 4.
Figure 17:
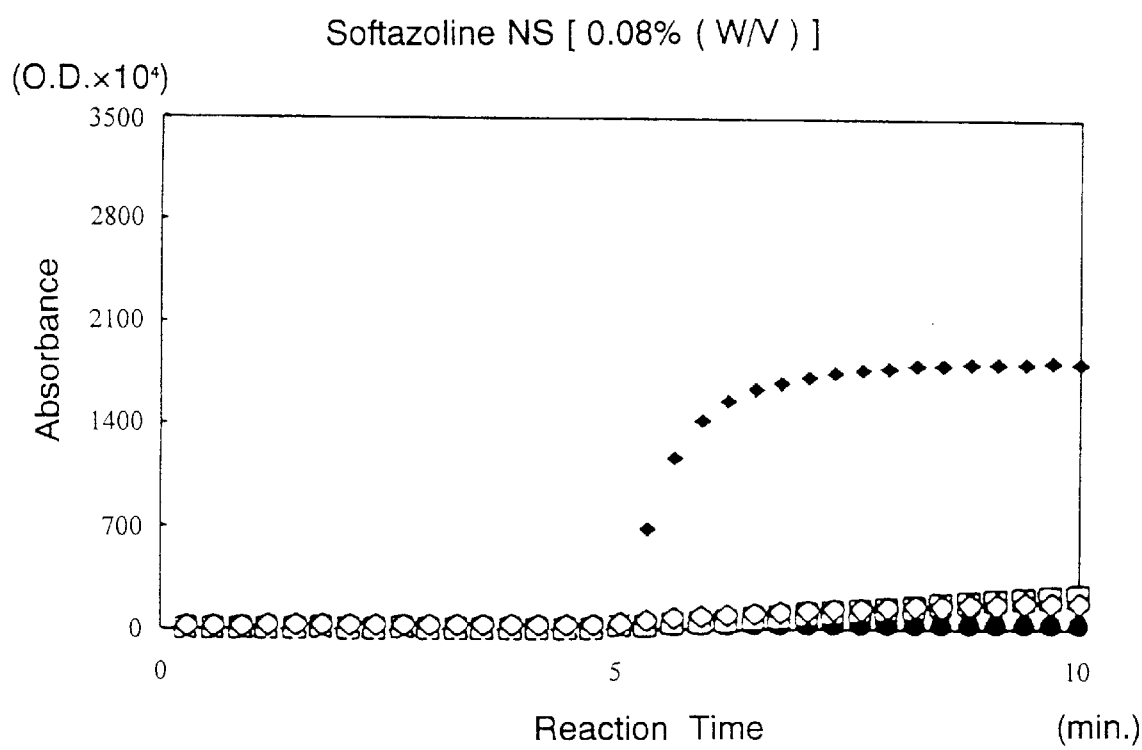
FIG. 17 Shows a reaction curve of various kind of samples containing various kinds of lipoproteins, which is obtained in Example 4.
Figure 18:
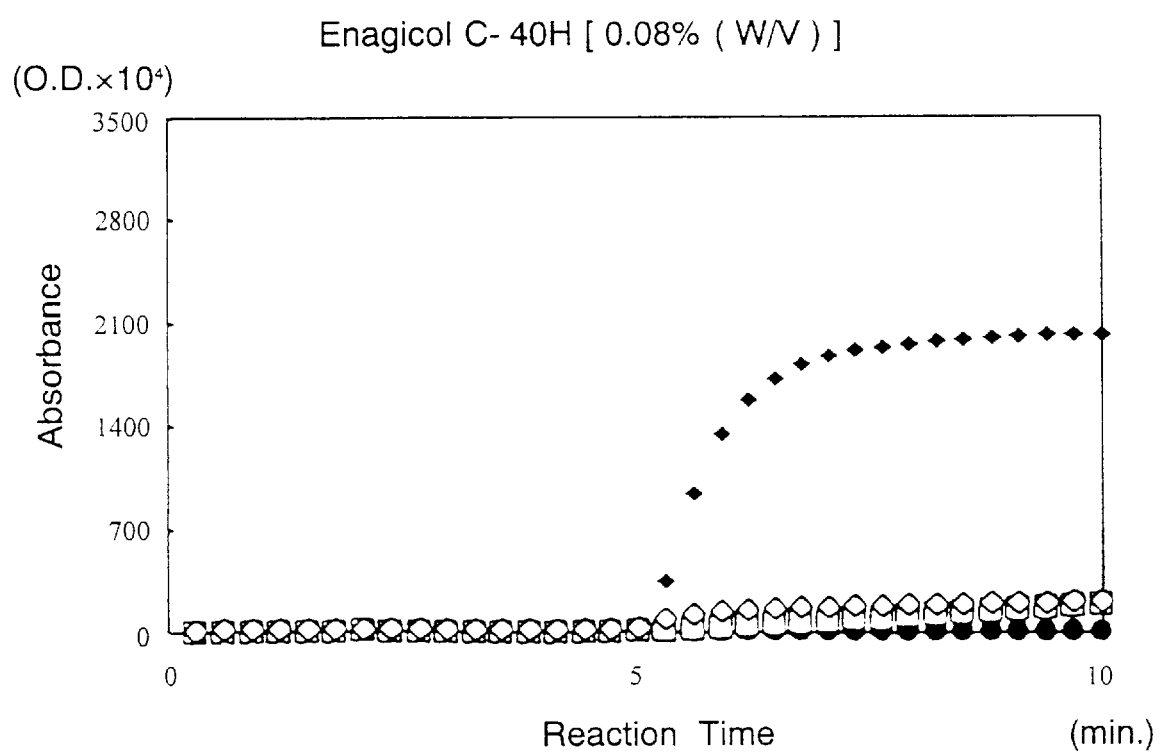
FIG. 18 Shows a reaction curve of various kind of samples containing various kinds of lipoproteins, which is obtained in Example 4.

The result of measurement using R-2 containing Softazoline CL as a surfactant, the result of measurement using R-2 containing Softazoline NS as a surfactant and the result of measurement using R-2 containing Enagicol C-40H as a surfactant are shown in FIG. 16, FIG. 17, and FIG. 18, respectively.

In FIG. 16 to 18, □ shows the result obtained in a sample containing HDL, ◆ shows the result obtained in a sample containing LDL, ◇ shows the result obtained in a sample containing VLDL, ▲ showed the result obtained in a sample containing CM and ● shows the result obtained in a sample containing no lipoprotein.

As clear from the measurement results in FIG. 16 to 18, it is understood that cholesterol in LDL can specifically be measured by measuring an amount of cholesterol in lipoproteins in the presence of an amphoteric surfactant and an aliphatic amine containing carboxyl group(s) or sulfonic acid group(s).

EXAMPLE 5

The typical examples of a kit for measuring an amount of LDL-cholesterol in a living sample such as plasma and serum are as follows.

(1) a first reagent (pH 6.5–7.5):
   one of a coupler and a developer,
   an aliphatic amine containing carboxyl group(s) or sulfonic acid group(s).

(2) a second reagent (pH 6.5–7.5):
   cholesterol oxidase,
   cholesterol esterase,
   peroxidase,
   the other of the coupler and the developer,
   an amphoteric surfactant,
   an aliphatic amine containing carboxyl group(s) or sulfonic acid group(s).

EXAMPLE 6

The typical examples of a kit for measuring an amount of LDL-cholesterol in a living sample such as plasma and serum are as follows.

(1) a first reagent (pH 6.5–7.5):
   an amphoteric surfactant,
   one of a coupler and a developer,
   an aliphatic amine containing carboxyl group(s) or sulfonic acid group(s).

(2) a second reagent (pH 6.5–7.5):
   cholesterol oxidase,
   cholesterol esterase,
   peroxidase,
   the other of the coupler and the developer,
   an aliphatic amine containing carboxyl group(s) or sulfonic acid group(s).

As mentioned above, the present invention is to provide a method for measuring an amount of LDL-cholesterol in a sample specifically at high accuracy and a reagent used in this method, and the present invention can attain such effect that direct measuring an amount of LDL-cholesterol by widely used automatic analyzers can be conducted by using the invention, which has not been possible after known methods, and thus the present invention gives great contribution in this kind of technical field.

What is claimed is:

1. A method for measuring an amount of cholesterol in low density lipoproteins, which comprises conducting the measurement of cholesterol in the presence of an amphoteric surfactant and an aliphatic amine containing carboxyl groups(s) or sulfonic acid group(s).

2. A method for measuring an amount of cholesterol in low density lipoproteins of a living sample, which comprises mixing the living sample with a first reagent comprising an aqueous medium, measuring an absorbance (OD1) of a resulting reaction solution, mixing the resulting solution with a second reagent solution containing a cholesterol oxidase and a cholesterol esterase, measuring an absorbance (OD2) of the latter resulting solution, subtracting a value obtained by multiplying OD1 with a correction coefficient from the OD2 to give OD3, applying thus obtained OD3 a calibration curve showing a relation between an amount of cholesterol and OD3 which is previously prepared by conducting the above process with the use of a standard specimen containing a predetermined amount of cholesterol, wherein each of an amphoteric surfactant and an aliphatic amine containing carboxyl group(s) or sulfonic acid group (s) is incorporated in at least one of the first reagent and the second reagent, and each of a coupler, a developer and a peroxidase is incorporated in at least one of the first reagent and the second reagent.

3. The method as claimed in claim 2, wherein one of the coupler and the developer is contained in the first reagent and the other is contained in the second reagent.

4. The method as claimed in claim 2, wherein the amphoteric surfactant is contained in the first reagent.

5. The method as claimed in claim 1 or 2, wherein the amphoteric surfactant is at least one selected from the group consisting of betaine derivatives, amino carboxylic acid derivatives, imidazoline derivatives and amine oxide derivatives.

6. The method as claimed in claim 1 or 2, wherein the aliphatic amine containing carboxyl group(s) or sulfonic acid group(s) is at least one selected from the group consisting of amino acids, aminoethanesulfonic acid derivatives, aminopropanesulfonic acid derivatives and glycine derivatives.

7. The method as claimed in claim 1 or 2, wherein the measurement is conducted in the absence of a nonionic surfactant.

8. A reagent for measuring an amount of cholesterol in low density lipoproteins, which comprises an amphoteric surfactant and an aliphatic amine containing carboxyl group (s) or sulfonic acid group(s).

9. The reagent as claimed in claim 8, wherein the reagent further comprises a cholesterol oxidase, a cholesterol esterase, a peroxidase and an oxidizable color forming reagent.

10. The reagent as claimed in claim 9, wherein the oxidizable color forming reagent comprises a coupler and a developer.

11. A kit for measuring an amount of cholesterol in low density lipoproteins, which comprises a first reagent containing one of a coupler and a developer and a second reagent containing a cholesterol oxidase, a cholesterol esterase, a peroxidase and the other of the coupler and the developer, wherein each of an amphoteric surfactant and an aliphatic amine containing carboxyl group(s) or sulfonic acid group(s) are incorporated in at least one of the first reagent and the second reagent.

12. A kit for measuring an amount of cholesterol in low density lipoproteins, which comprises a first reagent containing an amphoteric surfactant and one of a coupler and a developer and a second reagent containing a cholesterol oxidase, a cholesterol esterase, a peroxidase and the other of the coupler and the developer, wherein an aliphatic amine containing carboxyl group(s) or sulfonic acid group(s) are incorporated in at least one of the first reagent and the second reagent.

* * * * *